(12) United States Patent
Grodzki et al.

(10) Patent No.: US 10,143,853 B2
(45) Date of Patent: Dec. 4, 2018

(54) MAGNETIC RESONANCE METHOD AND APPARATUS FOR PLANNING A BRACHYTHERAPY TREATMENT USING AN IMAGE WITH HYPERINTENSE CONTRAST TO IDENTIFY THE POSITION OF A BRACHYTHERAPY APPLICATOR

(71) Applicant: Siemens Aktiengesellschaft, München (DE)

(72) Inventors: David Grodzki, Erlangen (DE); Sebastian Schmidt, Weisendorf (DE)

(73) Assignee: Siemens Aktiengesellschaft, Munich (DE)

(*) Notice: Subject to any disclaimer, the term of this patent is extended or adjusted under 35 U.S.C. 154(b) by 321 days.

(21) Appl. No.: 14/644,697

(22) Filed: Mar. 11, 2015

(65) Prior Publication Data
US 2015/0258349 A1 Sep. 17, 2015

(30) Foreign Application Priority Data
Mar. 11, 2014 (DE) .................... 10 2014 204 381

(51) Int. Cl.
*A61B 5/055* (2006.01)
*A61N 5/10* (2006.01)
(Continued)

(52) U.S. Cl.
CPC ............ *A61N 5/1039* (2013.01); *A61B 5/742* (2013.01); *A61N 5/1001* (2013.01);
(Continued)

(58) Field of Classification Search
None
See application file for complete search history.

(56) References Cited

U.S. PATENT DOCUMENTS

| | | | | |
|---|---|---|---|---|
| 5,510,713 A | * | 4/1996 | Bernstein ........... | G01R 33/4838 324/307 |
| 6,610,013 B1 | * | 8/2003 | Fenster ................. | A61N 5/103 600/439 |

(Continued)

OTHER PUBLICATIONS

Ma et al; "Change in T2-FAT Saturation MRI Correlates with Outcome in Cervical Cancer Patiens"; Int. J. Radiation Oncology Biol. Phys.; vol. 81; No. 5; pp. e707-e712; (2011).

(Continued)

*Primary Examiner* — Jonathan Cwern
(74) *Attorney, Agent, or Firm* — Schiff Hardin LLP

(57) ABSTRACT

In a method and system for planning a brachytherapy treatment, magnetic resonance image data of a patient are acquired by operating a magnetic resonance scanner according to a magnetic resonance sequence that designates an examination volume. An area of the patient is positioned in the examination volume such that the magnetic resonance image data contain at least a part of at least one applicator for the brachytherapy, which is located in the patient. The magnetic resonance sequence includes measurement parameters that lead to a contrast between the at least one applicator and surrounding tissue in the magnetic resonance image data. The position of the at least one applicator in the magnetic resonance image data is extracted, and a radiation treatment plan is created using the extracted position of the at least one applicator.

8 Claims, 4 Drawing Sheets

(51) Int. Cl.
*A61B 5/00* (2006.01)
*G01R 33/48* (2006.01)
*G01R 33/56* (2006.01)
*G01R 33/28* (2006.01)

(52) U.S. Cl.
CPC ..... *G01R 33/4828* (2013.01); *G01R 33/5607* (2013.01); *A61B 5/055* (2013.01); *A61B 2576/00* (2013.01); *G01R 33/286* (2013.01)

(56) References Cited

U.S. PATENT DOCUMENTS

| | | | |
|---|---|---|---|
| 2003/0107375 A1* | 6/2003 | McGee | G01R 33/285 324/307 |
| 2009/0234175 A1* | 9/2009 | Maier | A61N 5/1031 600/3 |
| 2010/0254897 A1* | 10/2010 | Frank | A61N 5/1027 424/1.29 |
| 2011/0012595 A1 | 1/2011 | Grodzki | |
| 2011/0115487 A1 | 5/2011 | Grodzki | |
| 2011/0116698 A1* | 5/2011 | Weis | G06K 9/6207 382/131 |
| 2011/0206260 A1* | 8/2011 | Bergmans | G01R 33/543 382/131 |
| 2012/0027278 A1 | 2/2012 | Chaney et al. | |
| 2013/0035588 A1 | 2/2013 | Shea et al. | |
| 2013/0317343 A1* | 11/2013 | Klimenko | A61B 5/055 600/411 |

OTHER PUBLICATIONS

Pernelle et al; "Validation of Catheter Segmentation for MR-guided Gynecolgic Cancer Brachytherapy"; MICCAI Konferenz 2013 (Medical Image Computing and Computer Assisted Interventions), Springer Verlag Berlin; vol. 16; No. 03; Author Manuscript; pp. 380-387; (2013).

Dolezel et al., "MRI-based pre-planning in patients with cervical cancer treated with three-dimensional brachytherapy," The British Journal of Radiology, vol. 84, pp. 850-856 (2011).

Jiménez De La Peña, "MRI-Brachytherapy of Cervical Carcinoma," Open Journal of Radiology, pp. 81-91 (2012).

* cited by examiner

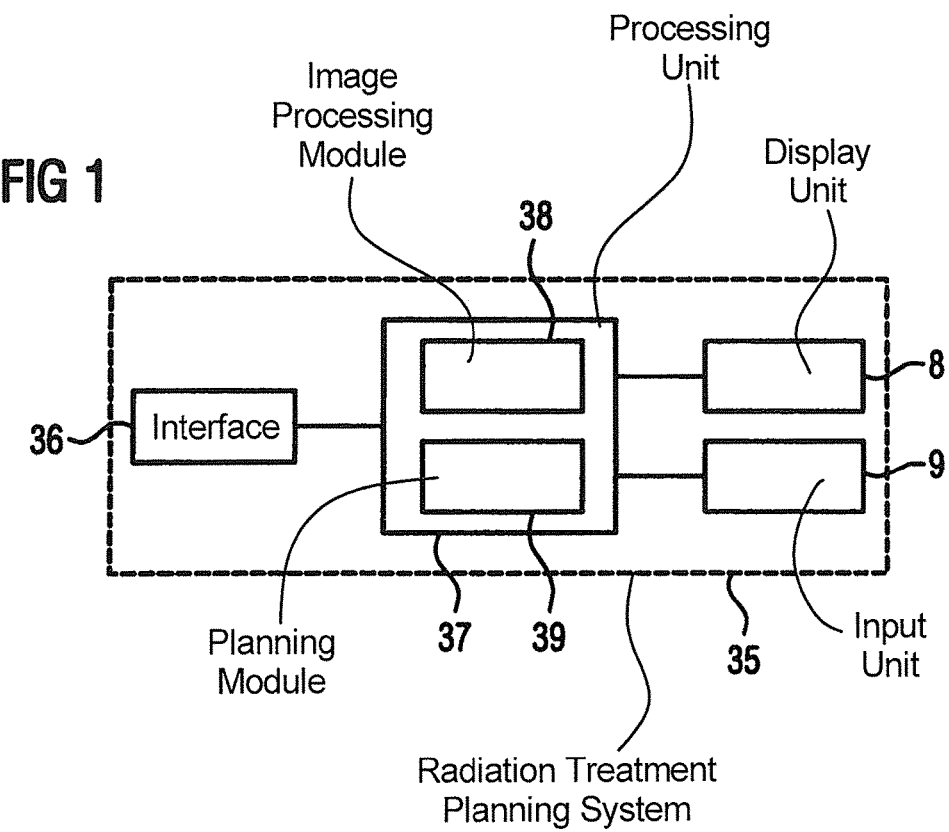

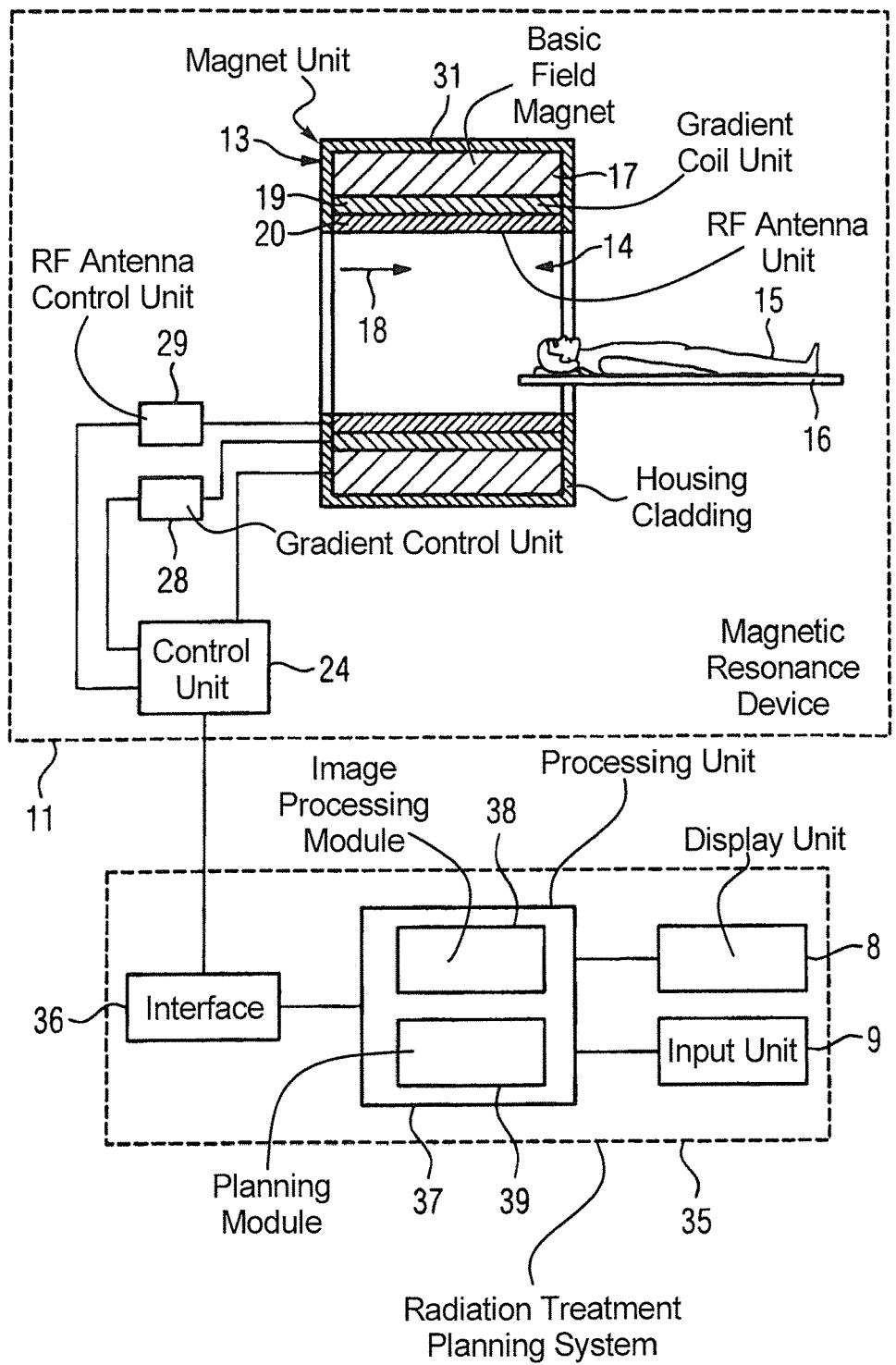

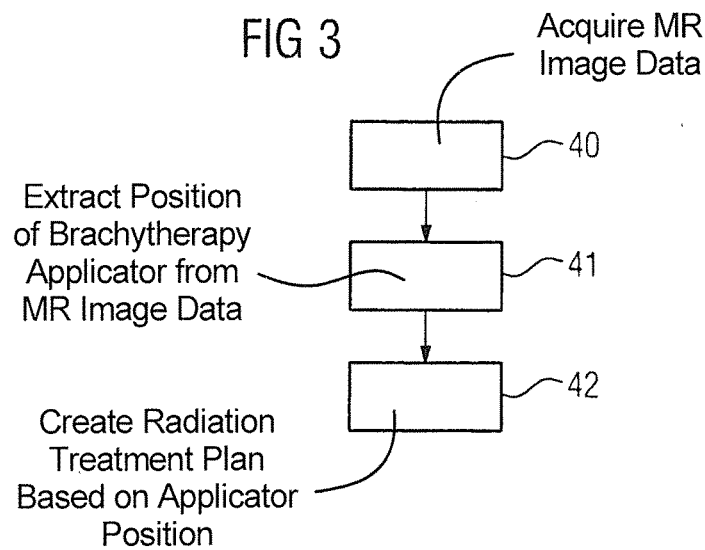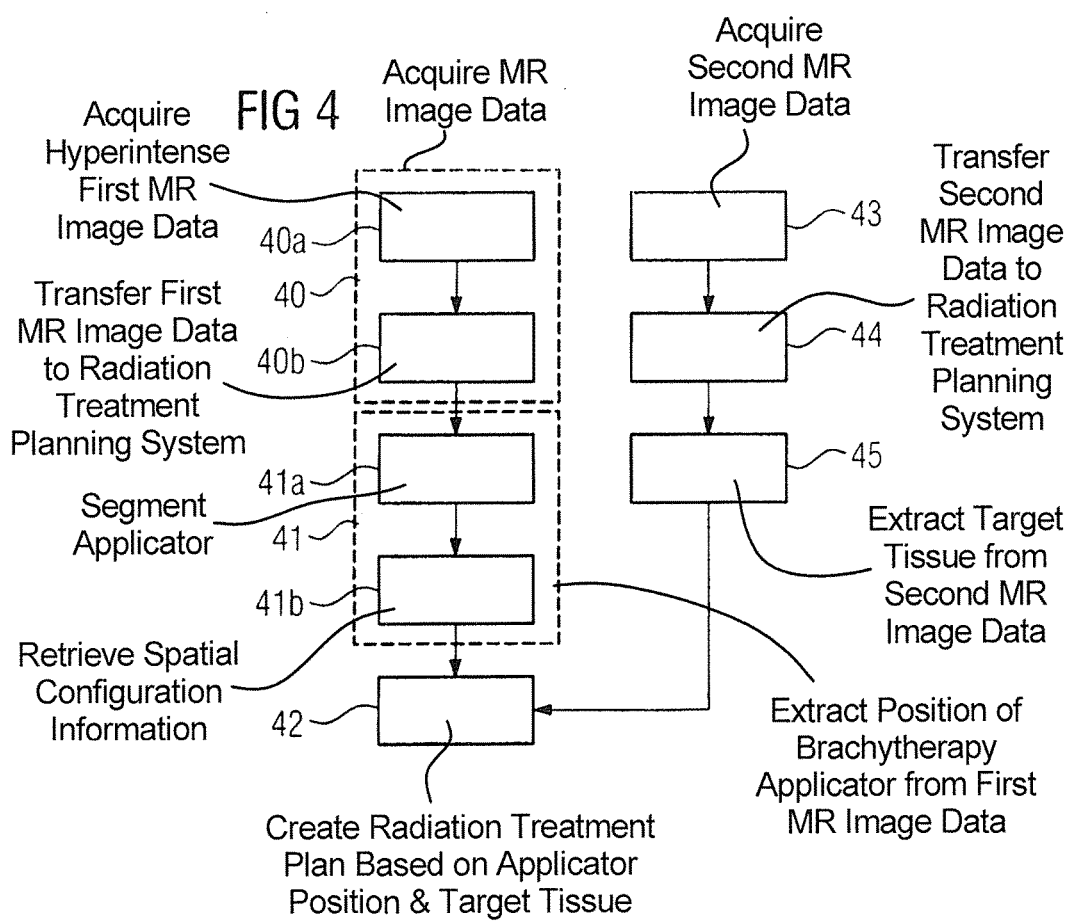

MAGNETIC RESONANCE METHOD AND APPARATUS FOR PLANNING A BRACHYTHERAPY TREATMENT USING AN IMAGE WITH HYPERINTENSE CONTRAST TO IDENTIFY THE POSITION OF A BRACHYTHERAPY APPLICATOR

BACKGROUND OF THE INVENTION

Field of the Invention

The invention relates to a method for planning a brachytherapy treatment and to a radiation treatment planning system.

Description of the Prior Art

In a brachytherapy, also called internal radiation therapy, short-distance radiation therapy or therapy with enclosed radiation sources, radiation sources that include radioactive substances are introduced into a patient's body in order to damage or destroy target tissue, for example tumors, by radiation locally in the patient's body. In such cases the radiation load for healthy tissue can be minimized because the radiation sources can contain radioactive substances with a short radiation range, for example beta radiators of gamma radiators of low energy. Furthermore the irradiation is carried out locally from within the body and does not, as is the case for example with an external radiation therapy by means of a linear accelerator, first have to penetrate through to the target tissue from outside the body through healthy tissue. The radiation sources are typically introduced into the body by means of at least one applicator, often by multiple applicators.

Radiation sources permanently implanted in the body can be used for brachytherapy. These permanently implanted radiation sources are typically implanted by applicators embodied as capsules, also called seeds, in the vicinity of the target tissue. This type of brachytherapy uses radiation sources having a low dose rate, typically below 2 Gray per hour. Such brachytherapy is also called Low-Dose-Rate brachytherapy (LDR brachytherapy).

As an alternative, at least one applicator embodied as a hollow needle and/or catheter can be implanted in the body in the vicinity of the target tissue for the brachytherapy. Temporary radiation sources, typically with a high dose rate, typically greater than 12 Gray per hour, can then be introduced through such a needle or catheter. This method is also called High-Dose-Rate brachytherapy (HDR brachytherapy).

For a brachytherapy treatment, especially when the at least one applicator is implanted in the body, a radiation treatment plan is typically created. This radiation treatment plan designates, for example, for how long and/or how often, in HDR brachytherapy, the radiation sources should remain in the vicinity of the target tissue. As an alternative or in addition, the radiation treatment plan can provide a recommendation for an implantation of further applicators, especially for an LDR brachytherapy. Naturally the radiation treatment plan can also provide for further measures appearing sensible to those skilled in the art.

A dose calculation, especially if the at least one applicator is already implanted into the body, is typically required for creating the radiation treatment plan. In such cases an especially precise knowledge about the position of the at least one applicator, especially in relation to the target tissue and/or surrounding tissue is required for the dose calculation. Surrounding tissue can include radiation-sensitive organs at risk (OAR), that are not intended for irradiation.

SUMMARY OF THE INVENTION

An object of the invention is to provide an improved planning of a brachytherapy treatment by the use of magnetic resonance imaging.

The inventive method for planning a brachytherapy treatment includes the following steps. Magnetic resonance image data of a patient are acquired by operating a magnetic resonance scanner with a magnetic resonance sequence that designates a first examination volume, wherein an area of the patient to be imaged is positioned in this examination volume such that the magnetic resonance image data represent at least a part of at least one applicator for the brachytherapy, which is located in the patient. The magnetic resonance sequence includes measurement parameters that produce a contrast between the at least one applicator and the surrounding tissue in the magnetic resonance image data. The position of the at least one applicator in first magnetic resonance image data is extracted. A radiation treatment plan is then created using the extracted position of the at least one applicator.

The magnetic resonance image data are acquired by a magnetic resonance scanner and/or a magnetic resonance imaging modality of a combined medical imaging device. The acquisition of the magnetic resonance image data is also called magnetic resonance imaging. In a magnetic resonance apparatus, also called a magnetic resonance tomography system, the body of the patient to be examined is usually exposed to a relatively high magnetic field, of 1.5 or 3 or 7 Tesla for example, produced by a basic field magnet. In addition, gradient pulses are emitted by a gradient coil system. Radio frequency pulses are then emitted via a radio-frequency antenna unit that has suitable antennas, which leads to the nuclear spins of specific atoms, excited resonantly by these radio frequency pulses, to be flipped by a defined flip angle in relation to the magnetic field lines of the basic magnetic field. During the relaxation of the nuclear spins, radio-frequency signals, called magnetic resonance signals, are emitted, which are received by suitable radio frequency antennas, and then further processed. From the raw data of an examination volume, the desired magnetic resonance image data of the examination volume can be reconstructed. Therefore a specific magnetic resonance sequence, also called a pulse sequence, is to be emitted for a specific magnetic resonance measurement, which consists of a sequence of radio frequency pulses, especially excitation pulses and refocusing pulses, as well as gradient pulses suitably coordinated thereto, that are emitted in different gradient axes in different spatial directions. Readout windows matching these in time are set, which specify the periods in which the induced magnetic resonance signals are acquired.

The at least one applicator is already located in the patient before the beginning of the acquisition of the magnetic resonance data. The at least one applicator is positioned in the vicinity of or directly on target tissue of the patient to be irradiated. The at least one applicator can be formed as a hollow needle and/or catheter. Then the at least one applicator typically has a surrounding wall that surrounds a hollow inner area. Radiation sources, especially for an HDR brachytherapy, can then be guided through the at least one applicator. As an alternative or in addition, the at least one applicator can be designed as a capsule (seed), which contains the radiation sources. This type of applicator is then typically implanted permanently in the body of the patient, especially for an LDR brachytherapy.

Because the magnetic resonance image data contains at least a part of the at least one applicator for the brachytherapy, this means that at least one part of the at least one applicator is visible in the magnetic resonance image data. The magnetic resonance image data can thus map an individual applicator, a number of applicators or all applicators. The at least one applicator can in such cases be mapped entirely in the magnetic resonance image data, or only partly. Preferably the part of the at least one applicator that is represented in the magnetic resonance image data is located in the vicinity of the target tissue.

The invention is based on the recognition that computed tomography images typically make it possible to determine relatively accurately the positions of applicators for brachytherapy, but typically have a bad soft tissue contrast. In magnetic resonance image data acquired by magnetic resonance sequences, a very good soft tissue contrast is typically present, so that, for example, target tissue can be distinguished especially easily from surrounding tissue in the magnetic resonance image data. In usual magnetic resonance sequences, which are designed to show anatomical features with different contrast, applicators are difficult to recognize, since the applicators typically cause a signal extinction and are thus difficult to distinguish from low-signal tissue. Thus in conventional magnetic resonance sequences, an automatic extraction of the position of the at least one applicator is difficult.

Therefore, in accordance with the invention, the magnetic resonance sequence has measurement parameters that are selected so as to cause the at least one applicator to be shown in the reconstructed image, because the selected measurement parameters lead to a contrast between the at least one applicator and surrounding tissue in the magnetic resonance image data. Advantageously the magnetic resonance sequence includes such measurement parameters that allow the magnetic resonance image data to make an especially advantageous presentation of the at least one applicator possible. For this purpose, the magnetic resonance sequence can be selected specifically to cause the material of the at least one applicator, which can be metal, for example, to be shown in the image. The at least one applicator thus stands out clearly in the magnetic resonance image data from surrounding tissue, for example the target tissue. The at least one applicator can also exhibit such a contrast with respect to the surrounding tissue that an edge area of the at least one applicator exhibits a contrast to the surrounding tissue.

Therefore the position of the at least one applicator in the magnetic resonance image data can be extracted especially easily. The extraction of the position of the at least one applicator can include a determination of a location and or a shape and or an alignment of the at least one applicator. To determine the location of the at least one applicator the magnetic resonance sequence can be measured in a number of spatial directions. Finally, based on knowledge of the position of the at least one applicator, especially with the inclusion of anatomical image information, the radiation treatment plan can be created. The radiation treatment plan can additionally be created on the basis of the known specific activity of the at least one radiation source, which is to be introduced into the at least one applicator, or is already introduced. Thus an especially advantageous radiation treatment planning for the brachytherapy by means of magnetic resonance imaging is possible by means of the inventive method. For example a dose distribution can be determined on the basis of the established position of the at least one applicator and information about a dose load of a radiation source located in at least one applicator. This can for example be superimposed in color onto an anatomical image.

In an embodiment of the method, the aforementioned magnetic resonance image data are first magnetic resonance image data, and second magnetic resonance image data of the patient are acquired by execution of a second magnetic resonance sequence by the scanner, and the creation of the radiation treatment plan ensues also using the second magnetic resonance image data. Thus the radiation treatment plan is advantageously created both on the basis of the first magnetic resonance image data and on the basis of the second magnetic resonance image data. The second magnetic resonance image data can in such cases provide valuable information in addition to the first magnetic resonance image data, which is useful or necessary for creation of the radiation treatment plan. Naturally any further magnetic resonance image data differing from the first magnetic resonance image data and the second magnetic resonance image data can be acquired, wherein the radiation treatment plan can then be created using the further magnetic resonance image data as well.

In an embodiment, the second magnetic resonance sequence designate a second examination volume, which is selected so that it at least partly coincides with the first examination volume. This means that the second examination volume overlaps spatially with the first examination volume. The second examination volume advantageously corresponds to the first examination volume. The correspondence of the first examination volume and the second examination volume enables the first magnetic resonance image data and the second magnetic resonance image data to be used in combination for creating the radiation treatment plan. The overlap of the first examination volume with the second examination volume can be used to harmonize the first magnetic resonance image data spatially with the second magnetic resonance image data. Thus on the basis of the overlap of the first examination volume with the second examination volume the at least one applicator in the first magnetic resonance image data can be put into a spatial relationship with anatomical structures from the second magnetic resonance image data.

In another embodiment, the second magnetic resonance sequence includes second measurement parameters that produce an anatomical contrast in the second magnetic resonance image data. For this purpose, the second magnetic resonance sequence can be, for example, a spin-echo sequence and/or a turbo spin-echo sequence and/or a gradient echo sequence and/or a further pulse sequence appearing sensible to those skilled in the art. The second magnetic resonance sequence in such cases is designed to better represent the anatomy of the patient than for representing the at least one applicator located in the patient. Thus the second magnetic resonance sequence can exhibit an especially marked soft tissue contrast for example. Thus the contrast between the target tissue and surrounding tissue can be more strongly marked in the second magnetic resonance image data than in the first magnetic resonance image data. In the magnetic resonance image data acquired by the second magnetic resonance sequence, the at least one applicator will then typically be represented as a signal extinction and/or low signal area, without contrast, or only with very low contrast to surrounding tissue. Therefore the first magnetic resonance sequence and the second magnetic resonance sequence advantageously have contrast mechanisms differing from one another.

In another embodiment, target tissue is segmented in the second magnetic resonance image data. The target tissue can be target structures in the body of the patient that are to be irradiated by the brachytherapy. For segmenting the target tissue in the second magnetic resonance image data, it is especially advantageous for the second magnetic resonance sequence to include measurement parameters that lead to an anatomical contrast, for example a T1-weighted or T2-weighted or diffusion-weighted contrast, in the second magnetic resonance image data. The target, tissue is thus represented especially clearly in the second magnetic resonance image data and can thus be segmented especially easily in the second magnetic resonance image data. Naturally organs at risk, which are to be avoided in the radiation treatment and/or are especially sensitive to radiation, can also be segmented in the second magnetic resonance image data. The first magnetic resonance image data and the second magnetic resonance image data are thus included differently in the radiation treatment plan. While the position of the at least one applicator is extracted on the basis of the first magnetic resonance image data, the second magnetic resonance image data can be used to segmenting the target tissue and/or the organs at risk. The target tissue can then be allocated a radiation dose in the radiation treatment planning. The organs at risk can then be allocated a maximum dose during the radiation treatment planning which may not be exceeded in the brachytherapy. Thus the first magnetic resonance image data and the second magnetic resonance image data supplement each other especially advantageously in the radiation treatment planning.

In another embodiment, the first measurement parameters lead to a hyperintense contrast of the at least one applicator in relation to the surrounding tissue in the first magnetic resonance image data. The first measurement parameters, for example, can lead to the hyperintense contrast of the at least one applicator in relation to target tissue and/organs at risk. The presence of the hyperintense contrast of the at least one applicator in relation to the surrounding tissue means in particular that the at least one applicator in the first magnetic resonance image data is shown brighter, meaning for example with higher grayscale values and/or higher signal strengths, than the surrounding tissue. The first magnetic resonance sequence thus includes such first measurement parameters that the at least one applicator is explicitly shown bright in the first magnetic resonance image data. Thus the position of the at least one applicator can be segmented especially easily for the creation of the radiation treatment plan. The at least one applicator has magnetic properties that can be known. The magnetic properties can include, for example, size and/or shape and/or composition of the at least one applicator. Thus the first measurement parameters of the first magnetic resonance sequence can be harmonized to the magnetic properties of the least one applicator. The effect of this can be that an especially advantageous, for example optimized, hyperintense contrast of the at least one applicator is present in relation to the surrounding tissue.

In order for the at least one applicator can be presented with a hyperintense contrast, the first magnetic resonance sequence is a so-called "white-iron" magnetic resonance sequence. Such a magnetic resonance sequence can explicitly present areas of the examination volume in which the magnetic field is changed, for example because of the presence of an applicator composed of metal, with a hyperintense contrast. Remaining areas, for example surrounding tissue such as target tissue or organs at risk, are typically presented by a white-iron magnetic resonance sequence as low-signal areas. If the first magnetic resonance sequence is a gradient echo sequence, then the first magnetic resonance sequence can have gradient dephasings for this purpose. As an alternative or in addition, the first magnetic resonance sequence properties can have the forms as described in the following two sections.

In one embodiment, the first magnetic resonance sequence includes at least one water saturation pulse, which causes a saturation of water tissue in the first magnetic resonance image data. A saturation pulse has the effect of setting a value of a magnetization, for example a longitudinal magnetization, in an examination volume substantially to zero. A saturation pulse in such cases is typically tissue-specific, meaning that a saturation pulse sets the magnetization only of a specific tissue type substantially to zero. For this purpose, such a saturation pulse can include a spoiler gradient for dephasing the magnetization. After the activation of a saturation pulse, only a transverse magnetization, especially for a specific tissue type, is still present. Saturation pulses thus can select the type of tissue from which magnetic resonance signals can be acquired. Water saturation pulses set the longitudinal magnetization of water tissue to zero (saturate it). In particular the at least one water saturation pulse should saturate the magnetization of water tissue, because the magnetization of water tissue, due to its significant different resonance frequency compared to material of the at least one applicator, is unaffected by the presence of the at least one applicator. The at least one water saturation pulse thus is preferably radiated at the resonant frequency of undisturbed water tissue. Thus the at least one water saturation pulse advantageously leads to a saturation of surrounding tissue relative to the at least one applicator and thus to a good contrast, particularly a hyperintense contrast, between the at least one applicator and the surrounding tissue. The at least one water saturation pulse is a component of a so-called "white-iron" magnetic resonance sequence and advantageously leads to the hyperintense contrast of the at least one applicator in relation to the surrounding tissue. For this purpose, the at least one water saturation pulse is advantageously combined with the at least one fat saturation pulse described in the following section.

In another embodiment, the first magnetic resonance sequence includes at least one fat saturation pulse, which has the effect of saturating fat (lipid) tissue in the first magnetic resonance image data. Fat saturation pulses set the longitudinal magnetization of fat tissue to zero (saturate it). A first magnetic resonance sequence with the at least one water saturation pulse and the at least one fat saturation pulse leads to hyperintense contrast of the at least one applicator in relation to the surrounding tissue. By means of the fat saturation, image contributions in the first magnetic resonance image data can be saturated that originate from fat tissue, and therefore do not represent the applicator. Thus the segmentation of the at least one applicator in the first magnetic resonance image data can be made easier. The at least one fat saturation pulse is an advantageous component of a so-called "white-iron" magnetic resonance sequence and leads to the hyperintense contrast of the at least one applicator in relation to the surrounding tissue. The at least one fat saturation pulse is advantageously combined with the at least one water saturation pulse described in the previous section.

In another embodiment, the first magnetic resonance image data include a number of slice images and the first measurement parameters to lead to a slice distance (spacing) between slice images of at least 5 mm. Thus the first magnetic resonance image data advantageously has a large slice distance. In particular the position of an applicator embodied tubular and/or needle-shaped can be determined especially easily on the basis of the first magnetic resonance image data with a large slice distance, especially of at least 5 mm. Advantageously just a few slices can also be used to determine the position of an applicator embodied in this way. Thus the first magnetic resonance image data can be acquired with little measurement effort and/or a short measurement time.

In another embodiment, the position of the at least one applicator is extracted in the first magnetic resonance image data by segmentation of the at least one applicator in the first magnetic resonance image data. Suitable segmentation algorithms known to those skilled in the art, for example a region-growing algorithm, can be used for the segmentation of the at least one applicator.

In another embodiment, information about the spatial configuration of the at least one applicator is stored in a database, and the position of the at least one applicator in the first magnetic resonance image data is extracted by retrieval and use of the information about the spatial configuration of the at least one applicator. For this purpose, the size and/or shape of the at least one applicator can be stored in the database. If different applicators are used, the sizes and/or shapes of the different applicators can be stored in the database. On the basis of the presentation of the at least one applicator in the first magnetic resonance image data, it can be recognized which of the different applicators is to be found in the patient. This recognition can occur automatically and/or by measuring the presentation of the at least one applicator in the first magnetic resonance image data. Naturally one of the different applicators can also be selected manually via an input unit. The size and/or shape of the recognized and/or selected at least one applicator can then be used for the extraction of the position of the at least one applicator. The user can also be provided with an image which presents the at least one applicator on the basis of the size and/or shape of the at least one applicator stored in the database. If there are a number of applicators in the patient, then to extract the positions of the number of applicators, the number of applicators in a subarea of the first magnetic resonance image data can be determined on the basis of geometrical distortions, for example the strength of the geometrical distortions of the first magnetic resonance image data.

The invention also concerns a radiation treatment planning system that includes an interface and a processing unit with an image processing module and a planning module.

The interface is designed to acquire (receive) magnetic resonance image data of a patient, by operation of a magnetic resonance scanner according to a magnetic resonance sequence. The first magnetic resonance sequence designates an examination volume, and an area of the patient to be imaged is positioned in the examination volume such that the magnetic resonance image data includes at least a part of at least one applicator for brachytherapy, which is situated in the patient. The magnetic resonance sequence includes measurement parameters that produce a contrast between the at least one applicator and surrounding tissue in the first magnetic resonance image data.

The image processing module is designed to extract the position of the at least one applicator in the magnetic resonance image data.

The planning module is designed to create a radiation treatment plan using the extracted position of the at least one applicator.

The image processing module in this case is provided with the magnetic resonance image data acquired via the interface, such that the image processing module can carry out a targeted analysis of the magnetic resonance image data for extracting the position of the at least one applicator. The interface and the processing unit with the image processing module and the planning module are thus designed to perform an inventive method.

In an embodiment of the radiation treatment planning system, the radiation treatment planning system includes a further interface that is designed to acquire second magnetic resonance image data of the patient which by execution of a second magnetic resonance sequence, and the planning module is designed to create the radiation treatment plan using the second magnetic resonance image data as well.

In an embodiment of the radiation treatment planning system, the image processing module is designed to process the first magnetic resonance image data and/or the second magnetic resonance image data. Advantageously the image processing module is matched for this purpose to the characteristics of the first magnetic resonance image data and/or of the second magnetic resonance image data.

Thus the second magnetic resonance sequence can have a second examination volume that coincides at least partly with the first examination volume. Then the image processing module can advantageously establish a correspondence between the first examination volume and the second examination volume.

A possible property of the second magnetic resonance image data is that the second magnetic resonance image data exhibits an anatomical contrast.

The image processing module can also segment target tissue in the second magnetic resonance image data.

A possible property of the first magnetic resonance image data is that the at least one applicator exhibits a hyperintense contrast in relation to the surrounding tissue in the first magnetic resonance image data. The first magnetic resonance image data can also exhibit a water saturation and/or a fat saturation. The first magnetic resonance image data can comprise a number of slice images with a slice spacing of at least 5 mm.

In an embodiment of the radiation treatment planning system, especially the image processing module, the position of the at least one applicator in the first magnetic resonance image data is extracted by a segmentation of the at least one applicator in the first magnetic resonance image data.

In another embodiment of the radiation treatment planning system, especially of the image processing module, information about a spatial configuration of the at least one applicator is stored in a database, and the position of the at least one applicator is extracted in the first magnetic resonance image data by retrieval and use of the information about the spatial configuration of the at least one applicator.

The advantages of the inventive radiation treatment planning system essentially correspond to the advantages of the inventive method that have been designed in detail above. Features, advantages or alternate embodiments described for the method are likewise applicable to the system.

BRIEF DESCRIPTION OF THE DRAWINGS

FIG. 1 shows an inventive radiation treatment planning system in a block diagram.

FIG. 2 shows an inventive radiation treatment planning system connected to a magnetic resonance device in a block diagram.

FIG. 3 is a flowchart of the first form of embodiment of an inventive method.

FIG. 4 is a flowchart of a second form of embodiment of an inventive method.

DESCRIPTION OF THE PREFERRED EMBODIMENTS

Figure 5:
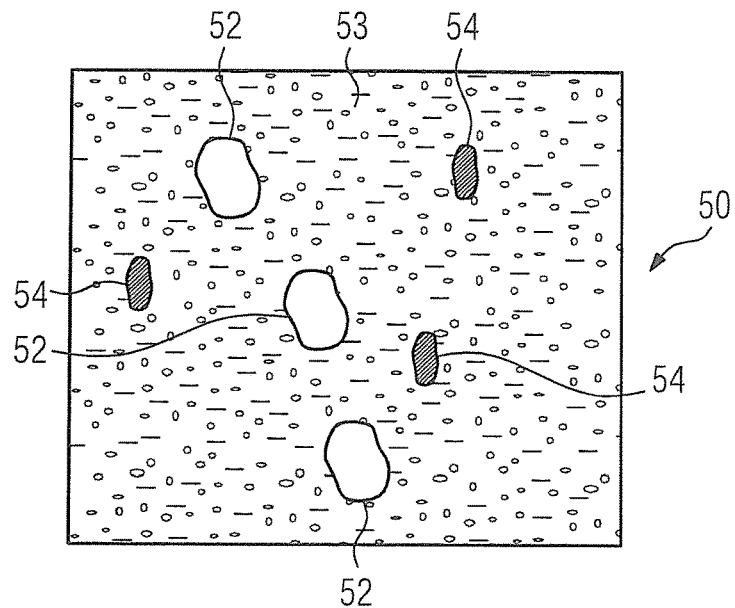
FIG. 5 illustrates second magnetic resonance image data acquired in accordance with the invention.

FIG. 1 is a block diagram of an inventive radiation treatment planning system 35 connected to a magnetic resonance device 11.

The radiation treatment planning system 35 comprises an interface 36, as well as a processing unit 37 with an image processing module 38 and the planning module 39. Furthermore the radiation treatment planning system 35 has a display unit 8 and an input unit 9. The radiation treatment planning system 35 is designed for carrying out an inventive method.

The interface 36 is embodied for acquiring first magnetic resonance image data of a magnetic resonance device 11. The radiation treatment planning system 35 can also have a further interface not shown in the diagram, for acquiring second magnetic resonance image data. The image processing module 38 is embodied for processing the first magnetic resonance image data acquired by means of the interface 36. For this the image processing module 38 is connected to the interface 36 for the purposes of exchanging data. The planning module 39 is embodied for creating a radiation treatment plan based on a result of the image processing module 38. For this the planning module 39 is connected to the image processing module 38 for the purposes of exchanging data. The radiation treatment plan can be displayed for a user on the display unit 8, for example a monitor and be processed by means of the input unit 9, for example a keyboard.

FIG. 2 shows a schematic diagram of an inventive radiation treatment planning system 35 connected to a magnetic resonance device 11. The description given below essentially restricts itself to the differences from the exemplary embodiment in FIG. 1, wherein, as regards components, features and functions which remain the same, the reader is referred to the description of the exemplary embodiment in FIG. 1. Components, features and functions which remain the same are basically labeled with the same reference numbers.

The magnetic resonance device 11 comprises a detector unit formed from a magnet unit 13 with a basic field magnet 17 for creating a strong and especially constant main magnetic field 18. In addition the magnetic resonance device 11 has a cylindrical patient receiving area 14 for receiving a patient 15, wherein the patient receiving area 14 is surrounded cylindrically in a circumferential direction by the magnet unit 13. The patient 15 can be pushed by means of a patient support apparatus 16 of the magnetic resonance device 11 into the patient receiving area 14. The patient support apparatus 16 has a support table for this purpose, which is disposed movably within the magnetic resonance device 11. The magnet unit 13 is shielded to the outside by means of housing cladding 31 of the magnetic resonance device.

The magnet unit 13 also has a gradient coil unit 19 for creating magnetic field gradients which are used for local encoding during imaging. The gradient coil unit 19 is controlled by means of a gradient control unit 28. Furthermore the magnet unit 13 has a radio-frequency antenna unit 20, which, in the case shown, is embodied as a body coil integrated permanently into the magnetic resonance device 11, and a radio-frequency antenna control unit for exciting a polarization, which is set in the main magnetic field 18 created by the basic field magnet 17. The radio-frequency antenna unit 20 is controlled by the radio-frequency antenna control unit 29 and irradiates radio-frequency magnetic resonance sequences into an examination area which is essentially formed by the patient receiving area 14. Thus the radio-frequency antenna unit 29 is designed for example for emitting water saturation pulses and fat saturation pulses. The radio-frequency antenna unit 20 is also embodied for receiving magnetic resonance signals, especially from the patient 15.

For controlling the basic field magnet 17, the gradient control unit 28 and the radio-frequency antenna control unit 29, the magnetic resonance device 11 has a control unit 24. The control unit 24 controls the magnetic resonance device 11 centrally, such as for example carrying out a predetermined imaging gradient echo sequence. Control information such as imaging parameters for example, as well as magnetic resonance image data reconstructed by means of the control unit 24, can be displayed for a user on a monitor of the magnetic resonance device 11 not shown in the diagram. In addition magnetic resonance device 11 has an input medium not shown in the diagram, by means of which information and/or parameters can be entered by a user during a measurement process. The control unit 24 can include the gradient control unit 28 and/or radio-frequency antenna control unit 29.

Reconstructed magnetic resonance image data can be transmitted from the control unit 24 of the magnetic resonance device 11 to the interface 36 of the radiation treatment planning system 35 and then be acquired by the interface 36. For this the interface 36 is connected in respect of an exchange of data to the magnetic resonance device 11, especially to the control unit 24 of the magnetic resonance device 11. The radiation treatment planning system 35 can then use the acquired magnetic resonance image data as a basis for the creation of a radiation treatment plan. The radiation treatment planning system 35 is thus designed, together with the magnetic resonance device 11, for executing an inventive method.

The magnetic resonance device 11 shown can of course include further components which magnetic resonance devices normally have. The basic functioning of a magnetic resonance device is known to those skilled in the art so that a more detailed description of further components need not be included herein.

FIG. 3 is a flowchart of a first embodiment of an inventive method for planning a brachytherapy treatment. In a first method step 40, a magnetic resonance device 11 acquires magnetic resonance image data of a patient 15 by means of a magnetic resonance sequence. The magnetic resonance sequence has an examination volume, wherein an area of the patient 15 to be mapped is positioned in the examination volume such that the magnetic resonance image data at least partly contain at least one applicator for the brachytherapy, which is located in the patient. The magnetic resonance sequence includes measurement parameters which lead to a contrast between the at least one applicator and surrounding tissue in the magnetic resonance image data.

In a further method step 41 the position of the at least one applicator in the magnetic resonance image data is extracted by means of the image processing module 38 of the processing unit 37 of the radiation treatment planning system 35.

In a further method step 42 a radiation treatment plan is created by means of the planning module 39 of the processing unit 37 of the radiation treatment planning system 35 using the extracted position of the at least one applicator. The radiation treatment plan can then for example be displayed on the display unit 8 of the radiation treatment planning system 35.

FIG. 4 shows a flowchart of a second embodiment of an inventive method. The description given below essentially restricts itself to the differences from the exemplary embodiment in FIG. 3, wherein, as regards components, features and functions which remain the same, the reader is referred to the description of the exemplary embodiment in FIG. 3. Components, features and functions which remain the same are basically labeled with the same reference numbers.

The second embodiment of the inventive method shown in FIG. 4 essentially includes the method steps 40, 41, 42 of the first embodiment of the inventive method according to FIG. 3. In addition, the second embodiment of the inventive method shown in FIG. 4 includes additional method steps and substeps. Also conceivable is an alternate method sequence to FIG. 4 which only has some of the additional method steps and/or substeps shown in FIG. 3. Naturally an alternate method sequence to FIG. 4 can also have additional method steps and/or substeps.

The first method step 40, the acquisition of the magnetic resonance (MR) image data, includes a first substep 40a, during which first magnetic resonance image data are acquired by operation of the magnetic resonance device 11. In this case first measurement parameters lead to a hyperintense contrast of the at least one applicator in relation to the surrounding tissue in the first magnetic resonance image data. For this purpose, a first magnetic resonance sequence is used that includes at least one water saturation pulse, which has the effect of saturating water tissue in the first magnetic resonance image data. Furthermore the first magnetic resonance sequence includes at least one fat saturation pulse, which has the effect of saturating fat tissue in the first magnetic resonance image data. The at least one water saturation pulse and the at least one fat saturation pulse are transmitted by the radio-frequency antenna unit 20 of the magnetic resonance device 11. The first magnetic resonance image data represent a number of slice images and the first measurement parameters lead to a slice spacing between the slice images of the first magnetic resonance image data of at least 5 mm.

The first method step 40 includes a second substep 40b, during which the first magnetic resonance image data are transmitted from the control unit 24 of the magnetic resonance device 11 to an interface 36 of the radiation treatment planning system 35 and are acquired by the interface 36, so that the first magnetic resonance image data can be further processed by the radiation treatment planning system 35.

The further method step 41, the extraction of the position of the at least one applicator, comprises a first substep 41a, during which a segmentation of the at least one applicator in the first magnetic resonance image data takes place. The further method step 41, the extraction of the position of the at least one applicator, includes a second substep 41b, during which information about the spatial configuration of the at least one applicator is retrieved from a database and used.

In a further method step 43, second magnetic resonance image data are acquired by execution of a second magnetic resonance sequence by the magnetic resonance device 11. The second magnetic resonance sequence has a second examination volume that coincides at least partly with the first examination volume. Furthermore the second magnetic resonance sequence includes second measurement parameters, which lead to an anatomical contrast in the second magnetic resonance image data. In a further method step 44 the second magnetic resonance image data are transferred to a further interface of the radiation treatment planning system 35. The processing unit 37 of the radiation treatment planning system 35 segments target tissue for the brachytherapy irradiation in the second magnetic resonance image data in step 45. This is especially easily possible in the second magnetic resonance image data, since said data has a high anatomical contrast. Finally the creation of the radiation treatment plan is carried out in the further method step 42 using the second magnetic resonance image data, especially on the basis of the segmented target tissue. Thus the first magnetic resonance image data and the second magnetic resonance image data advantageously supplement each other in the creation of the radiation treatment plan.

The method steps of the inventive method shown in FIG. 3 and FIG. 4 are carried out by the radiation treatment planning system 35. For this purpose the radiation treatment planning system 35 includes required software and/or computer programs which are stored in a memory unit of the radiation treatment planning system 35. The software and/or computer programs comprise program means which are designed to execute the inventive method when the computer program and/or the software is executed in the radiation treatment planning system 35 by means of a processing unit 37 of the radiation treatment planning system 35.

FIG. 5 shows a presentation of second magnetic resonance image data 50. In this case FIG. 5 serves to illustrate the contrast differences between fat tissue 52, 52a, water tissue 53, 53a and applicators 54, 54a in the second magnetic resonance image data 50.

The second magnetic resonance image data 50 exhibits an anatomical contrast. In the second magnetic resonance image data 50 fat tissue 52 is presented with a marked contrast to water tissue 53. The applicators 54 are merely shown as a signal extinction and are thus difficult to distinguish from fatty tissue 52 and/or water tissue 53. The second magnetic resonance image data 50 are thus, for example, suited to segmentation of target tissue. The positions of the applicators 54 can only be extracted with difficulty in the second magnetic resonance image data 50 because of the low contrast.

Figure 6:
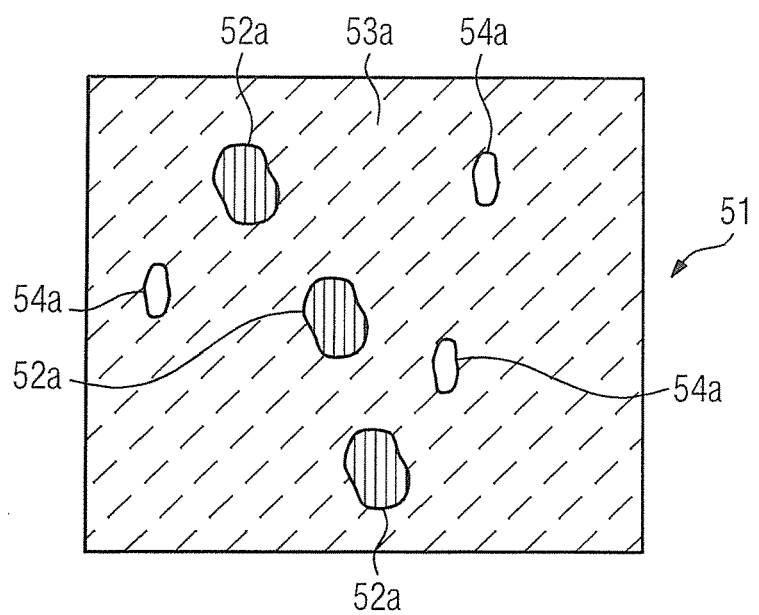
FIG. 6 illustrates first magnetic resonance image data acquired in accordance with the invention.

FIG. 6 shows a presentation of first magnetic resonance image data 51. In this case the FIG. 6 serves to illustrate the contrast differences between fatty tissue 52, 52a, water tissue 53, 53a and applicators 54, 54a in the first magnetic resonance image data 51.

The first magnetic resonance image data 51 exhibit a hyperintense contrast of the applicators 54a in relation to surrounding tissue, for example fat tissue 52a and/or water tissue 53a. The applicators 54a are thus brighter in the first magnetic resonance image data 51 than the fat tissue 52a and/or water tissue 53a. The reason for this is that the first magnetic resonance image data 51 has been acquired by execution of a first magnetic resonance sequence that uses at least one water saturation pulse and at least one fat saturation pulse.

Nuclear spins in the immediate vicinity of the applicators 54a are influenced by the presence of the applicators 54a, so that the at least one water saturation pulse and at least one fat saturation pulse do not saturate the spins in the immediate vicinity of the applicators 54a. Thus the at least one water saturation pulse and at least one fat saturation pulse only saturate the fatty tissue 52*a* and water tissue 53*a* in the first magnetic resonance image data 51. Thus the applicators 54*a* in the first magnetic resonance image data 51 are shown brighter than the fatty tissue 52*a* and/or water tissue 53*a*.

As a result of the hyperintense contrast the applicators 54*a* can be segmented especially easily in the first magnetic resonance image data 51 and the positions of the applicators 54*a* can be determined especially easily in the first magnetic resonance image data 51. Thus the first magnetic resonance image data 51 and the second magnetic resonance image data 50 supplement each other especially advantageously for the creation of a radiation treatment plan. In the first magnetic resonance image data 51, the positions of the applicators 54*a* can namely be determined especially simply and in the second magnetic resonance image data 50, the target tissue for the irradiation, for example fatty tissue 52, can be segmented especially easily.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for planning a brachytherapy treatment, comprising:
   using a computer to set measurement parameters of a single magnetic resonance sequence for a magnetic resonance scanner, in order to acquire magnetic resonance raw data from a patient having a brachytherapy applicator in the patient that delivers radiation to target tissue in the patient, said measurement parameters designating an examination volume, with a volume of the patient from which said magnetic resonance raw data are acquired being positioned in said examination volume so that said magnetic resonance raw data represent at least a portion of said brachytherapy applicator;
   also setting said measurement parameters for the execution of said single magnetic resonance sequence so that said single magnetic resonance sequence produces a hyperintense contrast in magnetic resonance image data, reconstructed from said magnetic resonance raw data, between said brachytherapy applicator and surrounding tissue in the patient and so that said single magnetic resonance sequence causes radiation of a radio-frequency (RF) water saturation pulse that saturates nuclear spins of water tissue in said surrounding tissue and radiation of an RF fat saturation pulse that saturates nuclear spins of fat tissue in said surrounding tissue;
   from said computer, operating said magnetic resonance scanner in order to execute said single magnetic resonance sequence, while the patient is situated in the magnetic resonance scanner so as to acquire said magnetic resonance raw data from said examination volume, said magnetic resonance raw data representing said hyperintense contrast and representing the saturated nuclear spins of water tissue in said surrounding tissue and saturated nuclear spins of fat tissue in said surrounding tissue;
   in said computer, reconstructing said magnetic resonance image data, forming a magnetic resonance image of said examination region, from said magnetic resonance raw data;
   in said computer, executing a segmentation algorithm that segments said brachytherapy applicator from said surrounding tissue, based on said hyperintense contrast in said magnetic resonance image, so as to automatically extract a position of said brachytherapy applicator in said magnetic resonance image;
   in said computer, generating a radiation treatment plan for the patient by executing a radiation treatment algorithm that requires identifying a dose of said radiation delivered to the patient by the brachytherapy applicator, and using the extracted position of the brachytherapy applicator to determine said dose in said algorithm; and
   presenting a visual representation of said radiation treatment plan at an output interface of said computer.

2. A method as claimed in claim 1 wherein said magnetic resonance raw data are first magnetic resonance raw data and said magnetic resonance image data are first magnetic resonance image data, and comprising operating said magnetic resonance scanner, while said patient with said brachytherapy applicator therein is situated in said magnetic resonance scanner, in order to execute a second magnetic resonance sequence, separately from said single magnetic resonance sequence, in order to acquire second magnetic resonance raw data, and providing said second magnetic resonance raw data to said computer and, in said computer, reconstructing second magnetic resonance image data, forming a second magnetic resonance image of said examination region, from said second magnetic resonance raw data, and generating said radiation treatment plan also using said second magnetic resonance image.

3. A method as claimed in claim 2 wherein said examination volume is a first examination volume, and comprising acquiring said second magnetic resonance raw data by operating said magnetic resonance scanner according to said second magnetic resonance sequence so as to acquire said second magnetic resonance raw data from a second examination volume that at least partially coincides with said first examination volume.

4. A method as claimed in claim 2 comprising setting measurement parameters of said second magnetic resonance sequence so as to produce an anatomical contrast of anatomy in the patient in said second magnetic resonance image data.

5. A method as claimed in claim 2 comprising, in said computer, automatically segmenting target tissue for said brachytherapy treatment in said second magnetic resonance image data.

6. A method as claimed in claim 1 comprising operating said magnetic resonance scanner according to said single magnetic resonance sequence so as to produce a plurality of slice images in said magnetic resonance image data, and setting said measurement parameters of said single magnetic resonance sequence to produce a slice spacing between said slice images of at least 5 mm.

7. A method as claimed in claim 1 comprising storing information describing a spatial configuration of said brachytherapy applicator in an electronic database that is accessible by said computer, and, in said segmentation algorithm, extracting said position of said brachytherapy applicator in said magnetic resonance image by retrieving and using said information describing said spatial configuration of said brachytherapy applicator.

8. A radiation treatment planning system comprising:
   a magnetic resonance scanner;
   a computer and a display in communication with said computer;
   said computer being configured to set measurement parameters of a single magnetic resonance sequence for said magnetic resonance scanner in order to acquire magnetic resonance raw data from a patient, having a brachytherapy applicator in the patient, said measurement parameters designating an examination volume, with a volume of the patient from which said magnetic resonance raw data are acquired being positioned in said examination volume so that said magnetic resonance raw data represent at least a portion of said brachytherapy applicator;

said computer being configured to also set said measurement parameters for the execution of said single magnetic resonance sequence so that said single magnetic resonance sequence produces a hyperintense contrast in magnetic resonance image data, reconstructed from said magnetic resonance raw data, between said brachytherapy applicator and surrounding tissue in the patient and so that said single magnetic resonance sequence causes radiation of a radio-frequency (RF) water saturation pulse that saturates nuclear spins of water tissue in said surrounding tissue and radiation of an RF fat saturation pulse that saturates nuclear spins of fat tissue in said surrounding tissue;

said computer being configured to operate said magnetic resonance scanner, while the patient is situated in the magnetic resonance scanner, in order to execute said single magnetic resonance sequence so as to acquire said magnetic resonance raw data from said examination volume, said magnetic resonance raw data representing said hyperintense contrast and representing the saturated nuclear spins of water tissue in said surrounding tissue and saturated nuclear spins of fat tissue in said surrounding tissue;

said computer being configured to reconstruct magnetic resonance image data, forming a magnetic resonance image of said examination region, from said magnetic resonance raw data;

said computer being configured to execute a segmentation algorithm that segments said brachytherapy applicator from said surrounding tissue, based on said hyperintense contrast in said magnetic resonance image, so as to automatically extract a position of said brachytherapy applicator in said magnetic resonance image;

said computer being configured to generate a radiation treatment plan for the patient by executing a radiation treatment algorithm that requires identifying a dose of said radiation delivered to the patient by the brachytherapy applicator, and to use the extracted position of the brachytherapy applicator to determine said dose in said algorithm; and said computer being configured to present a visual representation of said radiation treatment plan at said display.

* * * * *